(12) United States Patent
Simonnet et al.

(10) Patent No.: US 6,413,527 B1
(45) Date of Patent: Jul. 2, 2002

(54) NANOEMULSION BASED ON ALKYL ETHER CITRATES AND ITS USES IN THE COSMETICS, DERMATOLOGICAL, PHARMACOLOGICAL AND/OR OPHTHALMOLOGICAL FIELDS

(75) Inventors: Jean-Thierry Simonnet; Odile Sonneville, both of Paris; Sylvie Legret, Chatillon, all of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/478,408

(22) Filed: Jan. 6, 2000

(30) Foreign Application Priority Data

Jan. 14, 1999 (FR) ............................................ 99 00408

(51) Int. Cl.$^7$ ............................ A61K 6/00; A61K 7/00; A61F 2/00
(52) U.S. Cl. ..................... 424/401; 424/400; 424/422; 424/427; 514/844; 514/845; 514/846; 514/912; 514/937; 514/938
(58) Field of Search .................. 424/70.11, 70.19, 424/70.28, 78.03, 59, 60, 69, 400, 401, 402, 450; 514/544, 773, 778; 510/122, 123, 125, 126, 417

(56) References Cited

U.S. PATENT DOCUMENTS

| | | | | |
|---|---|---|---|---|
| 4,797,273 A | * | 1/1989 | Linn et al. ..................... 424/59 |
| 5,523,025 A | * | 6/1996 | Erilli ............................ 252/550 |
| 5,556,628 A | * | 9/1996 | Derian et al. ................ 424/410 |
| 5,576,279 A | * | 11/1996 | Pyles ........................... 510/122 |
| 5,710,114 A | * | 1/1998 | Pyles ........................... 510/123 |
| 5,716,418 A | * | 2/1998 | Matzik et al. ................... 8/406 |
| 5,871,762 A | * | 2/1999 | Venkitataman et al. ...... 424/402 |
| 5,919,487 A | * | 7/1999 | Simonnet et al. ............ 424/490 |
| 5,925,341 A | * | 7/1999 | Cervantes et al. ........ 424/78.03 |
| 6,120,778 A | * | 9/2000 | Simonnet ..................... 424/401 |
| 6,162,448 A | * | 12/2000 | Nguyen et al. .............. 424/401 |

FOREIGN PATENT DOCUMENTS

| | | |
|---|---|---|
| EP | 0 842 652 | 5/1998 |
| EP | 0 852 941 | 7/1998 |

* cited by examiner

Primary Examiner—Thurman K. Page
Assistant Examiner—Charesse L. Evans
(74) Attorney, Agent, or Firm—Oblon, Spivak, McClelland, Maier & Neustadt, P.C.

(57) ABSTRACT

A nanoemulsion, the oil globules of which have an average size of less than 100 nm, comprising an anionic surfactant chosen from alkyl ether citrates and at least one oil having a molecular weight of greater than 400, the ratio by weight of the amount of oily phase to the amount of surfactant ranging from 2 to 10. The emulsion obtained is transparent and stable on storage. It can comprise large amounts of oil while retaining good transparency and while having good cosmetic properties. It can constitute a composition for topical use, a pharmaceutical composition or an ophthalmological composition. The invention also relates to the use of the nanoemulsion according to the invention in the cosmetics and dermatological fields, in particular for moisturizing the skin and/or mucous membranes, as well as for treating the hair, and in the ophthalmological field, as an eye lotion for treating the eyes.

27 Claims, No Drawings

NANOEMULSION BASED ON ALKYL ETHER CITRATES AND ITS USES IN THE COSMETICS, DERMATOLOGICAL, PHARMACOLOGICAL AND/OR OPHTHALMOLOGICAL FIELDS

BACKGROUND OF THE INVENTION

1. Field of the Invention

The present invention relates to a nanoemulsion based on an anionic surfactant chosen from alkyl ether citrates and on at least one oil having a molecular weight of greater than 400, the ratio by weight of the amount of oily phase to the amount of surfactant ranging from 2 to 10. The invention also relates to a process for the preparation of the said nanoemulsion and to its uses, in particular in the cosmetics, dermatological and/or ophthalmological fields. This nanoemulsion is stable on storage and can comprise large amounts of oil while retaining good transparency and while having good cosmetic properties.

2. Background of the Invention

Nanoemulsions are oil-in-water emulsions, the oil globules of which have a very fine particle size, that is to say a number-average size of less than 100 nm. They are generally manufactured by mechanical fragmentation of an oily phase in an aqueous phase in the presence of a surfactant. In the case of nanoemulsions, the very small size of the oily globules is obtained in particular by virtue of at least one pass through a high-pressure homogenizer. The small size of the globules confers on them cosmetically advantageous properties which distinguish them from conventional emulsions: they are transparent and exhibit a novel texture. They can also carry active agents more efficiently.

Transparent microemulsions are known in the state of the art. In contrast to nanoemulsions, microemulsions are not, strictly speaking, emulsions; they are transparent solutions of micelles swollen by oil, which oil is generally a very-short-chain oil (e.g. hexane or decane) and is solubilized by virtue of the joint presence of a significant amount of surfactants and of cosurfactants which form the micelles. The size of the swollen micelles is very small owing to the small amount of oil which they can solubilize. This very small size of the micelles is the cause of their transparency, as with nanoemulsions. However, in contrast to nanoemulsions, microemulsions are spontaneously formed by mixing the constituents, without contributing mechanical energy other than simple magnetic stirring. The major disadvantages of microemulsions are related to their high proportion of surfactants, leading to intolerance and resulting in a sticky feel during application to the skin. Furthermore, their formulation range is generally very narrow and their temperature stability very limited.

In addition, nanoemulsions are known in the state of the art comprising an amphiphilic lipid phase composed of phospholipids, water and oil. These emulsions exhibit the disadvantage of being unstable on storage at conventional storage temperatures, namely between 0 and 45° C. They lead to yellow compositions and produce rancid smells which develop after several days of storage.

Nanoemulsions stabilized by a lamellar liquid crystal coating, obtained by the combination of a hydrophilic surfactant and of a lipophilic surfactant, are also known. However, these combinations are problematic to prepare. Furthermore, the nanoemulsions obtained exhibit a waxy and film-forming feel which is not very pleasant for the user.

Furthermore, EP-A-728,460 discloses nanoemulsions based on fluid non-ionic amphiphilic lipids. However, these nanoemulsions exhibit the disadvantage of having a sticky effect during application to the skin.

The need therefore remains for nanoemulsions which have neither the disadvantages of those of the prior art nor the disadvantages of microemulsions.

SUMMARY OF THE INVENTION

The present inventors have now discovered, unexpectedly, that the use of an anionic surfactant chosen from alkyl ether citrates and of at least one oil having a molecular weight of greater than 400 (=400 grams per mole) makes it possible to obtain novel nanoemulsions exhibiting all the advantages of known nanoemulsions without their disadvantages.

Accordingly, the present invention provides a nanoemulsion, comprising:

an oily phase dispersed in an aqueous phase and having oil globules with a number-average size of less than 100 nm, at least one anionic surfactant selected from the group consisting of alkyl ether citrates, and at least one oil having a molecular weight of greater than 400, where the ratio by weight of the amount of oily phase to the amount of surfactant is 2 to 10.

The present invention also provides a composition suitable for topical application comprising the inventive nanoemulsion.

The present invention also provides an ophthalmic vehicle comprising the inventive nanoemulsion.

The present invention also provides a pharmaceutical composition comprising the inventive nanoemulsion.

The present invention also provides a method of caring for, treating and/or making up the skin, face and/or scalp, comprising applying the inventive nanoemulsion to the skin, face and/or scalp.

The present invention also provides a method of caring for and/or treating the hair, comprising applying the inventive nanoemulsion to the hair.

The present invention also provides a method of caring for and/or moisturizing the skin, mucous membranes and/or scalp, comprising applying the inventive nanoemulsion to the skin, mucous membranes and/or scalp.

The present invention also provides a method of making the inventive nanoemulsion, comprising combining the oily phase, aqueous phase and anionic surfactant.

The present invention also provides a method of making the inventive nanoemulsion, comprising:

mixing the aqueous phase and the oily phase with vigorous stirring at an ambient temperature ranging from 10 to 80° C. and then homogenizing the mixture at a pressure ranging from $6 \times 10^7$ Pa to $18 \times 10^7$ Pa.

A more complete appreciation of the invention and many of the attendant advantages thereof will be readily obtained as the same becomes better understood by reference to the following detailed description.

DETAILED DESCRIPTION OF THE INVENTION

The nanoemulsions according to the invention generally have a transparent to bluish appearance. Their transparency is measured by a transmittance coefficient at 600 nm ranging from 10 to 90% or else by a turbidity ranging from 60 to 600 NTU and preferably from 70 to 300 NTU, where the turbidity is measured with a Hach Model 2100 P portable turbidimeter. This range for the transmittance coefficient includes all specific values and subranges therebetween, such as 20, 30, 50, 75, 80 and 85%. This range for the turbidity includes all specific values and subranges therebetween, such as 75, 100, 150, 200 and 250 NTU.

The oil globules of the nanoemulsions of the invention have a number-average size of less than 100 nm and preferably ranging from 20 to 75 nm and more preferably from 40 to 60 nm. The decrease in the size of the globules makes it possible to promote the penetration of the active principles into the surface layers of the skin (carrier effect). This size range includes all specific values and subranges therebetween, such as 25, 35, 50, 60, 70, 80 and 90 nm.

The anionic surfactant which can be used in the nanoemulsion of the invention is chosen from alkyl ether citrates and mixtures thereof. In a specific embodiment of the invention, the nanoemulsion of the invention can be devoid of any surfactant other than the alkyl ether citrates.

The alkyl ether citrates which can be used as surfactants in the nanoemulsion according to the invention can be selected in particular from the group consisting of the monoesters, diesters or triesters formed by citric acid and at least one oxyethylenated fatty alcohol comprising a saturated or unsaturated, linear or branched alkyl chain having from 8 to 22 carbon atoms and comprising from 3 to 9 oxyethylene groups, and mixtures thereof. In fact, a mixture of one or more of these citrates can be used in the nanoemulsion of the invention.

These citrates can be chosen, for example, from the mono-, di- and triesters of citric acid and of ethoxylated lauryl alcohol comprising from 3 to 9 oxyethylene groups sold by Witco under the name Witconol EC, in particular Witconol EC 2129, which is predominantly a dilaureth-9 citrate, and Witconol EC 3129, which is predominantly a trilaureth-9 citrate.

The alkyl ether citrates used as surfactants are preferably employed in the neutralized form at a pH of approximately 7, the neutralization agent being chosen from inorganic bases, such as sodium hydroxide, potassium hydroxide or ammonia, and organic bases, such as mono-, di- and triethanolamine, aminomethyl- 1,3-propanediol, N-methylglucamine, basic amino acids, such as arginine and lysine, and their mixtures.

The amount of surfactant in the nanoemulsion of the invention can range, for example, from 0.2 to 15% by weight and preferably from 1 to 8% by weight with respect to the total weight of the nanoemulsion. This range for the amount of surfactant includes all specific values and subranges therebetween, such as 0.5, 1, 2, 5, 10 and 12% by weight.

The ratio by weight of the amount of the oily phase to the amount of surfactant ranges from 2 to 10 and preferably from 3 to 6, inclusive of all specific values and subranges therebetween, such as 4, 5 and 8. The term "amount of oily phase" is understood here to mean the total amount of the constituents of this phase without including the amount of surfactant.

The nanoemulsion according to the invention comprises at least one oil with a molecular weight of greater than 400. The oils with a molecular weight of greater than 400 can be chosen from oils of animal or vegetable origin, mineral oils, synthetic oils and silicone oils, and their mixtures. Mention may be made, as oils of this type, of, for example, isocetyl palmitate, isocetyl stearate, avocado oil or jojoba oil.

In addition, the oily phase can optionally comprise other oils and in particular oils having a molecular weight of less than 400. These oils are also chosen from oils of animal or vegetable origin, mineral oils, synthetic oils and silicone oils. Mention may be made, for example, as oils with a molecular weight of less than 400, of isododecane, isohexadecane, volatile silicone oils, isopropyl myristate, isopropyl palmitate or $C_{11}$–$C_{13}$ isoparaffin.

The oily phase can also comprise fatty substances other than the oils indicated above, such as fatty alcohols, for example stearyl, cetyl and behenyl alcohols, fatty acids, for example stearic, palmitic and behenic acids, oils of fluorinated type, waxes, gums and mixtures thereof.

The nanoemulsions in accordance with the invention comprise an amount of oily phase preferably ranging from 2 to 40% and better still from 5 to 30% by weight with respect to the total weight of the nanoemulsion, the proportion of oil(s) having a molecular weight of greater than 400 preferably representing at least 40% by weight of the oily phase.

According to a specific embodiment of the invention, the nanoemulsion of the invention additionally comprises one or more ionic amphiphilic lipids.

The ionic amphiphilic lipids which can be used in the nanoemulsions of the invention are preferably selected from the group formed by anionic amphiphilic lipids and alkylsulfonic derivatives.

The anionic amphiphilic lipids can be more particularly selected from the group formed by:
  the alkaline salts of dicetyl and dimyristyl phosphate;
  the alkaline salts of cholesterol sulphate;
  the alkaline salts of cholesterol phosphate;
  lipoamino acids and their salts, such as mono- and disodium acylglutamates, such as the disodium salt of N-stearoyl-L-glutamic acid sold under the name Acylglutamate HS21 by Ajinomoto;
  the sodium salts of phosphatidic acid;
  phospholipids.

The alkylsulfonic derivatives can more particularly be chosen from the alkylsulfonic derivatives of formula (I):

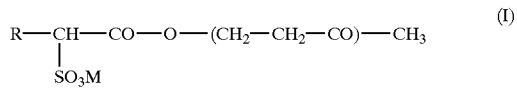

(I)

in which R represents an alkyl radical comprising from 16 to 22 carbon atoms, in particular the $C_{16}H_{33}$ and $C_{18}H_{37}$ radicals, taken as a mixture or separately, and M is an alkali metal, such as sodium.

According to a preferred embodiment of the invention, a lipoamino acid is used as ionic amphiphilic lipid.

The ionic amphiphilic lipids can be introduced into one or other phase of the nanoemulsion. When they are present in the nanoemulsion of the invention, they can be used in concentrations preferably ranging from 0.01 to 5% by weight and more particularly from 0.25 to 1% by weight with respect to the total weight of the nanoemulsion.

The emulsions in accordance with the present invention can comprise additives for improving the transparency of the formulation.

These additives are preferably selected from the group formed by:
  lower alcohols comprising from 1 to 8 carbon atoms and more particularly from 2 to 6 carbon atoms, such as ethanol;
  glycols, such as glycerol, propylene glycol, 1,3-butylene glycol, dipropylene glycol, pentylene glycol, isoprene glycol and polyethylene glycols comprising from 4 to 16 and preferably from 8 to 12 ethylene oxide units;

sugars, such as glucose, fructose, maltose, lactose or sucrose.

These additives can be used as a mixture. When they are present in the nanoemulsion of the invention, they can be used at concentrations preferably ranging from 0.01 to 30% by weight with respect to the total weight of the nanoemulsion and better still from 5 to 20% by weight with respect to the total weight of the nanoemulsion. The amount of alcohol(s) and/or of sugar(s) preferably ranges from 5 to 20% by weight with respect to the total weight of the nanoemulsion and the amount of glycol(s) preferably ranges from 5 to 15% by weight with respect to the total weight of the nanoemulsion.

In addition, the use of the alcohols as defined above at concentrations greater than or equal to 15% by weight makes it possible to obtain preservative-free emulsions.

The nanoemulsions defined above can be used in any field where this type of composition is useful, as will be readily appreciated by those skilled in the art. They can constitute in particular compositions for topical use and in particular cosmetic or dermatological compositions. They can also be used as ophthalmic vehicles. In addition, they can constitute, in the pharmaceutical field, a pharmaceutical composition which can be administered orally, parenterally or transcutaneously.

Another aspect of the invention is therefore a composition for topical use, characterized in that it comprises a nanoemulsion as defined above. A composition for topical or pharmaceutical use comprises a physiologically acceptable medium, i.e., compatible with the skin, mucous membranes, scalp, eyes and/or hair.

Another aspect of the invention is an ophthalmic vehicle, which comprises a nanoemulsion as defined above.

Another aspect of the invention is a pharmaceutical composition, which comprises a nanoemulsion as defined above.

The nanoemulsions of the invention can comprise water-soluble or fat-soluble active agents having a cosmetic, dermatological, ophthalmic or pharmaceutical activity. The fat-soluble active principles are in the oily globules of the emulsion, whereas the water-soluble active principles are in the aqueous phase of the emulsion. Mention may be made, by way of examples of cosmetic active agents, of vitamins, such as vitamin E, and their derivatives and in particular their esters, provitamins, such as panthenol, humectants and sun-screen agents.

Mention may be made, as ophthalmic active agents, of, for example, antiglaucoma agents, such as betaxolol; antibiotics, such as acyclovir; antiallergics; anti-inflammatory agents, such as ibuprofen and its salts, diclofenac and its salts, or indomethacin; or antiviral agents.

The nanoemulsions in accordance with the invention can be provided in the form of a lotion, serum, cream, milk or toilet water and can comprise adjuvants commonly used in the cosmetics, dermatological and ophthalmic fields, such as, for example, gelling agents, preservatives, antioxidants and fragrances. They can also be provided in the form of an eye lotion, in particular for ophthalmological applications.

Mention may be made, among the gelling agents which can be used, of cellulose derivatives, algal derivatives, natural gums and synthetic polymers, such as polymers and copolymers of carboxyvinyl acids, for example those sold under the name Carbopol by Goodrich.

Another aspect of the invention is a process for the preparation of a nanoemulsion as defined above, this process comprising the mixing of the aqueous phase and the oily phase with vigorous stirring at a temperature ranging from 10 to 80° C. and then a homogenization of the mixture at a pressure preferably ranging from $6 \times 10^7$ Pa to $18 \times 10^7$ Pa (high-pressure homogenization). The shearing preferably ranges from $2 \times 10^6$ s$^{-1}$ to $5 \times 10^8$ s$^{-1}$ and better still from $1 \times 10^8$ s$^{-1}$ to $3 \times 10^8$ s$^{-1}$ (s$^{-1}$ signifies second$^{-1}$).

The nanoemulsion of the invention can be used, for example, for caring for, treating or making up the skin, face and/or scalp.

Another subject-matter of the invention is therefore the cosmetic use of the nanoemulsion as defined above for caring for, treating and/or making up the skin, face and/or scalp.

In addition, the nanoemulsion of the invention can also be used for caring for and/or treating the hair. It makes it possible to obtain a deposit of oil on the hair, which renders the latter glossier and more resistant to styling, without, however, making it lank. It also makes it possible, as a pretreatment, to improve the effects of dyeing or permanent waving.

Another subject-matter of the invention is therefore the cosmetic use of the nanoemulsion as defined above for caring for and/or treating the hair.

The nanoemulsion according to the invention makes possible in particular good moisturizing of the skin, mucous membranes and/or scalp and is particularly suited to the treatment of dry skin.

Another subject-matter of the invention is therefore a cosmetic process for caring for and/or moisturizing the skin, mucous membranes and/or scalp, characterized in that a nanoemulsion as defined above is applied to the skin, mucous membranes and/or scalp.

The invention also relates to the use of the nanoemulsion according to the invention in the manufacture of a dermatological composition intended for the treatment of dry skin.

Finally, the invention also relates to the use of the nanoemulsion according to the invention in the manufacture of an ophthalmological composition.

In each of these uses described above, the nanoemulsion, or a composition containing the same, is applied to the area to be treated. Such methods of application are well-known to those of skill in the art.

EXAMPLES

Having generally described this invention, a further understanding can be obtained by reference to certain specific examples which are provided herein for purposes of illustration only and are not intended to be limiting unless otherwise specified. The amounts shown are as % by weight.

Example

Fluid Make-Up Remover

| Oily phase: | |
|---|---|
| Disodium salt of N-stearoyl-L-glutamic acid (Acylglutamate HS21 from Ajinomoto) | 0.5% |
| Isocetyl stearate (M.W. = 508) | 10% |
| Isopropyl myristate (M.W. = 270) | 5% |
| Aqueous phase: | |
| Witconol 3129 (Witco) | 4.5% |
| NaOH (1N) | 0.5% |

| | |
|---|---|
| Glycerol | 5% |
| Dipropylene glycol | 10% |
| Water | 64.5% |

A transparent nanoemulsion is obtained, the size of the globules of which is 54 nm and the turbidity of which is 214 NTU.

Obviously, numerous modifications and variations of the present invention are possible in light of the above teachings. It is therefore to be understood that within the scope of the appended claims, the invention may be practiced otherwise than as specifically described herein.

This application is based on French Patent Application Serial No. 9900408, filed on Jan. 14, 1999, and incorporated herein by reference in its entirety.

What is claimed is:

1. A nanoemulsion, comprising:
 an oily phase dispersed in an aqueous phase and having oil globules with a number-average size of less than 100 nm,
 at least one anionic surfactant selected from the group consisting of alkyl ether citrates, and
 at least one oil having a molecular weight of greater than 400,
 wherein the ratio by weight of the amount of oily phase to the amount of surfactant is 2 to 10.

2. The nanoemulsion of claim 1, having a turbidity ranging from 60 to 600 NTU.

3. The nanoemulsion of claim 1, wherein the amount of surfactant ranges from 0.2 to 15% by weight with respect to the total weight of the nanoemulsion.

4. The nanoemulsion of claim 1, wherein the ratio by weight of the amount of oily phase to the amount of surfactant ranges from 3 to 6.

5. The nanoemulsion of claim 1, wherein the oil globules have an average size ranging from 20 to 75 nm.

6. The nanoemulsion of claim 1, wherein the surfactant is selected from the group consisting of the monoesters, diesters or triesters formed by citric acid and at least one oxyethylenated fatty alcohol comprising a saturated or unsaturated, linear or branched alkyl chain having from 8 to 22 carbon atoms and comprising from 3 to 9 oxyethylene groups, and mixtures thereof.

7. The nanoemulsion of claim 1, wherein the surfactant is selected from the group consisting of the mono-, di- and triesters of citric acid and of ethoxylated lauryl alcohol comprising from 3 to 9 oxyethylene groups, and mixtures thereof.

8. The nanoemulsion of claim 1, further comprising at least one neutralization agent selected from the group consisting of inorganic bases, organic bases and mixtures thereof.

9. The nanoemulsion of claim 1, wherein the oil with a molecular weight of greater than 400 is selected from the group consisting of oils of animal or vegetable origin, mineral oils, synthetic oils and silicone oils, and mixtures thereof.

10. The nanoemulsion of claim 1, wherein the oily phase further comprises at least one oil having a molecular weight of less than 400.

11. The nanoemulsion of claim 1, wherein the oily phase comprises at least 40% by weight of oil(s) having a molecular weight of greater than 400 with respect to the total weight of the oily phase.

12. The nanoemulsion of claim 1, wherein the amount of oily phase ranges from 2 to 40% by weight with respect to the total weight of the nanoemulsion.

13. The nanoemulsion of claim 1, further comprising at least one ionic amphiphilic lipid selected from the group consisting of anionic amphiphilic lipids and alkylsulfonic derivatives.

14. The nanoemulsion of claim 13, wherein the ionic amphiphilic lipids are selected from the group consisting of
 the alkaline salts of dicetyl and dimyristyl phosphate;
 the alkaline salts of cholesterol sulphate;
 the alkaline salts of cholesterol phosphate;
 the salts of lipoamino acids;
 the sodium salts of phosphatidic acid;
 phospholipids;
 the alkylsulfonic derivatives of formula (I):

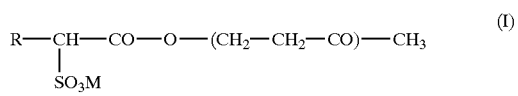

in which R represents $C_{16}$–$C_{22}$ alkyl radicals, taken as a mixture or separately, and M is an alkali metal; and mixtures thereof.

15. The nanoemulsion of claim 13, wherein the amount of ionic amphiphilic lipid(s) ranges from 0.01 to 5% by weight with respect to the total weight of the nanoemulsion.

16. The nanoemulsion of claim 1, further comprising an additive which improves the transparency selected from the group consisting of lower alcohols, glycols, sugars and mixtures thereof.

17. The nanoemulsion of claim 16, wherein the additive is present in a concentration ranging from 5 to 20% by weight with respect to the total weight of the nanoemulsion.

18. The nanoemulsion of claim 1, wherein it comprises a cosmetic, dermatological, ophthalmological or pharmaceutical active agent.

19. A composition suitable for topical application comprising the nanoemulsion of claim 1.

20. An ophthalmic vehicle, comprising the nanoemulsion of claim 1.

21. A pharmaceutical composition, comprising the nanoemulsion of claim 1.

22. A method of caring for, treating and/or making up the skin, face and/or scalp, comprising applying the nanoemulsion of claim 1 to the skin, face and/or scalp.

23. A method of caring for and/or treating the hair, comprising applying the nanoemulsion of claim 1 to the hair.

24. A method of caring for and/or moisturizing the skin, mucous membranes and/or scalp, comprising applying the nanoemulsion of claim 1 to the skin, mucous membranes and/or scalp.

25. A method of making the nanoemulsion of claim 1, comprising combining the oily phase, aqueous phase and anionic surfactant.

26. A method of making the nanoemulsion of claim 1, comprising:
 mixing the aqueous phase and the oily phase with vigorous stirring at an ambient temperature ranging from 10 to 80° C. and then homogenizing the mixture at a pressure ranging from $6 \times 10^7$ Pa to $18 \times 10^7$ Pa.

27. The method of claim 26, wherein the mixing of the oily phase and the aqueous phase occurs under a shear ranging from $2 \times 10^6$ s$^{-1}$ to $5 \times 10^8$ s$^{-1}$.

* * * * *